(12) United States Patent
Schima et al.

(10) Patent No.: US 8,897,873 B2
(45) Date of Patent: Nov. 25, 2014

(54) FLOW ESTIMATION IN A BLOOD PUMP

(75) Inventors: Heinrich Schima, Vienna (AT); Ing Francesco Moscato, Vienna (AT); Marcus Granegger, Vienna (AT)

(73) Assignee: HeartWare, Inc., Miami Lakes, FL (US)

( * ) Notice: Subject to any disclaimer, the term of this patent is extended or adjusted under 35 U.S.C. 154(b) by 13 days.

(21) Appl. No.: 13/533,437

(22) Filed: Jun. 26, 2012

(65) Prior Publication Data

US 2013/0030240 A1 Jan. 31, 2013

Related U.S. Application Data

(60) Provisional application No. 61/501,496, filed on Jun. 27, 2011.

(51) Int. Cl.
*A61N 1/365* (2006.01)
*A61M 1/10* (2006.01)
*A61M 1/12* (2006.01)

(52) U.S. Cl.
CPC ........... *A61M 1/1086* (2013.01); *A61M 1/1031* (2014.02); *A61M 1/122* (2014.02); *A61M 1/101* (2013.01); *A61M 2205/3334* (2013.01)
USPC ......................................................... 607/17

(58) Field of Classification Search
USPC .................................................... 600/17, 16
See application file for complete search history.

(56) References Cited

U.S. PATENT DOCUMENTS

| | | | |
|---|---|---|---|
| 6,066,086 A * | 5/2000 | Antaki et al. | 600/17 |
| 6,866,625 B1 | 3/2005 | Ayre et al. | |
| 2003/0223879 A1 | 12/2003 | Yanai et al. | |
| 2004/0039243 A1 * | 2/2004 | Bearnson et al. | 600/16 |
| 2005/0214131 A1 * | 9/2005 | Miles et al. | 417/44.11 |
| 2006/0222533 A1 * | 10/2006 | Reeves et al. | 417/420 |
| 2007/0282298 A1 | 12/2007 | Mason et al. | |
| 2009/0064755 A1 | 3/2009 | Fleischli et al. | |
| 2011/0077782 A1 | 3/2011 | Miyakoshi et al. | |

OTHER PUBLICATIONS

International Search Report issued by the International Searching Authority (ISA/US) on Sep. 17, 2012 in connection with International Application No. PCT/US2012/44243.

Written Opinion of the International Searching Authority issued by the International Searching Authority (ISA/US) on Sep. 17, 2012 in connection with International Application No. PCT/US2012/44243.

Malagutti et al., "Noninvasive Average Flow Estimation for an Implantable Rotary Blood Pump: A New Algorithm Incorporating the Role of Blood Viscosity", Artificial Organs 2007; 31(1):45-52.

* cited by examiner

*Primary Examiner* — Christopher D Koharski
*Assistant Examiner* — Jeremiah Kimball
(74) *Attorney, Agent, or Firm* — Lerner, David, Littenberg, Krumholz & Mentlik, LLP

(57) ABSTRACT

The flow rate of blood out of a blood pump is determined at least in part based on an acceleration of the pump's rotor and on the blood's viscosity. Considering the rotor acceleration when determining blood flow rate, increases the accuracy of the blood flow measurement thereby permitting the determination of a parameter related to the contractility of a patient's heart. The parameter may include a rate of pressure change of blood across the pump, a ratio of the rate of pressure change and a peak-to-peak value of the blood flow rate, or any other contractility index.

21 Claims, 8 Drawing Sheets

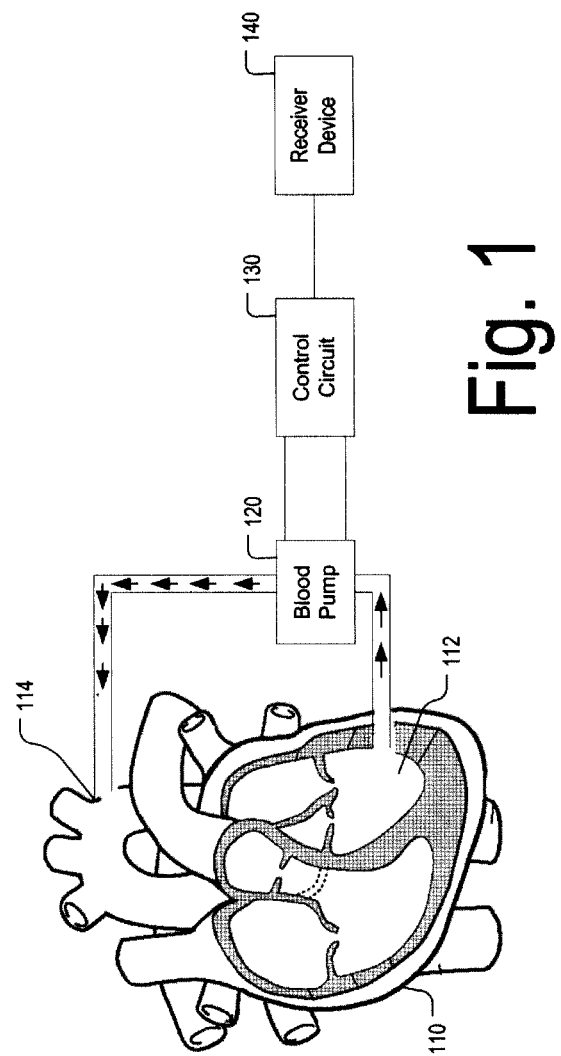

FLOW ESTIMATION IN A BLOOD PUMP

CROSS-REFERENCE TO RELATED APPLICATIONS

The present application claims the benefit of the filing date of U.S. Provisional Patent Application No. 61/501,496, filed Jun. 27, 2011, the disclosure of which is hereby incorporated herein by reference.

FIELD OF THE INVENTION

The present invention relates to blood pumps, to methods of using blood pumps, and to control circuits adapted for use with blood pumps.

BACKGROUND OF THE INVENTION

Implantable blood pumps may be used to provide assistance to patients with late stage heart disease. Blood pumps operate by receiving blood from a patient's vascular system and impelling the blood back into the patient's vascular system. By adding momentum and pressure to the patient's blood flow, blood pumps may augment or replace the pumping action of the heart. For example, a blood pump may be configured as ventricular assist device or "VAD." Where a VAD is used to assist the pumping action of the left ventricle, the device draws blood from the left ventricle of the heart and discharges the blood into the aorta.

To provide clinically useful assistance to the heart, blood pumps must impel blood at a substantial blood flow rate. For an adult human patient, a ventricular assist device may be arranged to pump blood at about 1-10 liters per minute at a pressure differential across the pump of about 10-110 mm Hg, depending on the needs of the patient. The needs of the patient may vary with age, height, and other factors.

BRIEF SUMMARY OF THE INVENTION

One aspect of the invention provides an implantable blood pump system. The system comprises a pump and a control circuit. The pump includes a housing having an axis, and a rotor disposed within the housing. The control circuit is operatively coupled to the pump and configured to determine various parameters related to the operation of the pump, such as amount of current used to drive the pump, a speed of a rotor that is part of the pump, and an acceleration of the rotor. The control circuit is further configured to determine a flow rate of blood leaving the pump based at least in part on the acceleration of the pump's rotor.

Considering the pump rotor's acceleration when estimating the blood flow rate increases the accuracy of the estimation. The increased accuracy results in the estimate that reflects with greater precision dynamic transients in the blood flow that are caused by the pumping action of a patient's heart. The increased precision facilitates the use of the blood flow rate in monitoring the condition of a patient's heart.

In another aspect of the invention, a method is provided for controlling a blood pump for providing ventricular assistance to patients with heart disease. The method desirably comprises determining the amount of current that is used to drive the pump, the speed of a rotor of the pump, and an acceleration of the rotor. The method further includes determining the flow rate of blood exiting the pump based at least in part on the determined amount of current, speed, and rotor acceleration. In some instances, the method may further include determining a parameter related to the contractility of a patient's heart based on the determined blood flow rate. The parameter may be based on a rate of pressure change of blood across the pump or the ratio of the rate of pressure change and a peak-to-peak value of the blood flow rate estimate.

BRIEF DESCRIPTION OF THE DRAWINGS

FIG. 1 is a schematic, partially sectional view of a blood pump system in accordance with one embodiment of the invention.

DETAILED DESCRIPTION

Figure 2A:
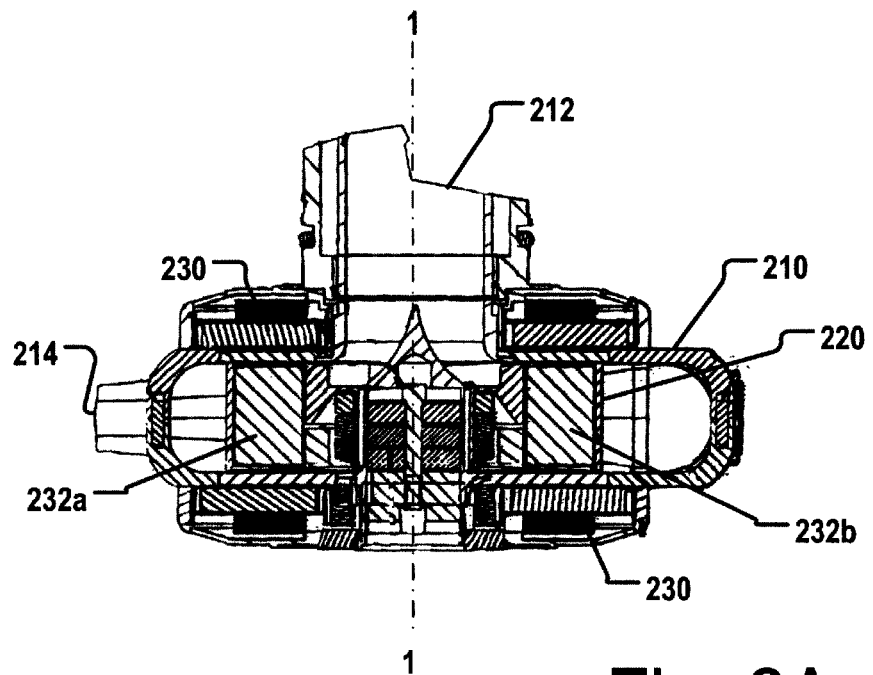
FIG. 2A is a diagrammatic sectional view of a blood pump.

A blood pump system 100 (FIG. 1) includes a blood pump 120, a control circuit 130, and a receiver device 140. The pump 120 is a centrifugal pump, such as HVAD manufactured by Heartware Inc. in Miami Lakes, Fla., USA. The HVAD pump is further discussed in U.S. PG Pub. 2007/0280841, titled "Hydrodynamic Thrust Bearings for Rotary Blood Pumps," the disclosure of which is incorporated by reference herein. In operation, the blood pump 120 draws blood from the left ventricle 112 of a patient's heart 110 and propels the blood through an outflow graft connected to the patient's ascending aorta 114. Although in this example, the blood pump 120 is a centrifugal pump, in other examples it may be an axial flow pump, or any other pump suitable for providing vascular assistance.

The control circuit 130 includes hardware and software for controlling the various aspects of the operation of the pump 120. The control circuit 130 is coupled to the pump 120 and it is operable to collect pump data. The pump data includes speed of rotation of the pump's 120 rotor and amount of current used to drive the pump. In addition, the control circuit 130 is operable to estimate the flow rate of blood exiting the pump 120 when the pump is used to propel blood from the heart's 110 left ventricle into the aorta. The estimate is generated using an improved model for the estimation of blood flow rate. In one aspect, for example, the model determines blood flow rate based in part on the acceleration of the rotor 220 of the pump 120 (shown in FIG. 2) and possibly the viscosity of the patient's blood. Using this model results in the estimate having a dynamic range of 15 Hz.

The 15 Hz dynamic range of the blood flow rate estimate enables dynamic transients imparted on the flow rate by the pulsating action of the heart 110 to be discernible from the estimate. For example, if a graph of the flow estimate versus time is displayed on a receiver device 140, the graph will provide a good approximation of the action of the heart 110 with time. A physician can examine such a graph visually to evaluate the condition of the heart 110. In addition, the blood flow rate estimate can be usable as a basis for determining a parameter related to the contractility of the heart 110. The parameter may be the maximum rate of pressure change (Dp/dt max) across the pump 120, a contractility index that is defined as the ratio of Dp/dt max and the blood flow's peak to peak value, or any other type of contractility index. The parameter may be determined by the receiver device 140.

The receiver device may be a laptop, or any other device capable of displaying text or an image, or playing a sound based on blood flow rate estimates. The receiver device 140 may be connected to the blood control circuit 130 via a data connection, such as USB or Bluetooth. In one example, the receiver device is operable to process one or more blood flow rate estimates received from the control circuit 130 and determine a parameter related to contractility of the heart 110. Afterwards, the receiver device 140 may output the determined parameter using an electronic display, such as an LCD screen. As yet another example, a sound may be generated based on the parameter. By way of example, a low-pitched sound may be played when the value of the parameter falls below a threshold and a high-pitched sound may be placed when the parameter value exceeds another threshold. Alternatively, the parameter may be presented in a time-plot, or another suitable representation. In another example, the time-plot of the flow rate of blood exiting the pump 120 may be presented in a time plot. In either instance, the information output by the receiver device 140 may be viewed by a clinician when evaluating the health of the heart 110. In that regard, the controller of the pump 120, in conjunction with the receiver device 140, may be used as a device for determining information about the health of the patient's heart 110. Stated another way, the control circuit 130 can gather dynamic flow data without the need for additional instrumentation.

As noted, determining the parameter related to contractility is made possible by the presence of the dynamic transients in the flow rate of blood leaving the pump 120 that are created by the pulsating action of the heart 110. Every time the heart contracts, the outflow of blood from the pump 120 accelerates and every time the heart dilates the flow of blood slows down. Because the dynamic transients tend to be relatively fast-changing, the dynamic range of the blood flow rate estimate made by the control circuit 130 has to be at least 15 Hz in order for the transients to be discernible from the estimate. Such dynamic range permits the detection of maximum rate of pressure change (Dp/dt max) across the pump 120 of up to 2300 mmHg/s. Detecting of up to 2300 mmHg/s pressure change rate is sufficient for the purposes of evaluating the contractility of the heart 110 as a sound ventricle develops up to 2000 mmHg/s of pressure change when it contacts.

Figure 2B:
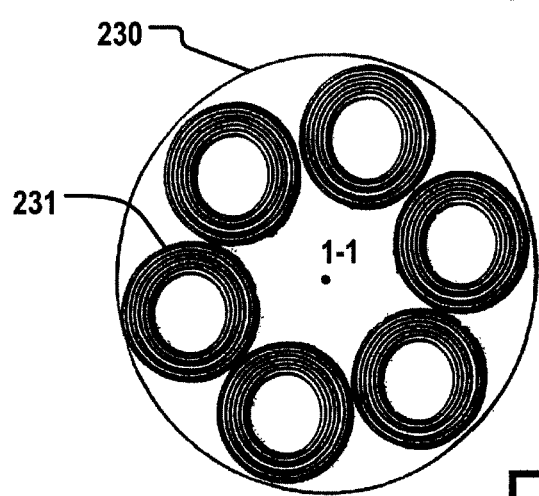
FIG. 2B is a diagrammatic sectional view of a stator of the blood pump.

FIG. 2A depicts a cross-section of the pump 120. As illustrated, the blood pump 120 includes a housing 210 defining a pumping chamber and a rotor 220 disposed within the pumping chamber. The rotor 220 includes permanent magnets 232*a-b*. The rotor includes an impeller configured to push blood that enters the housing through the inflow tube 212 out of the outflow tube 214. The pump also includes stators 230 disposed above and below the rotor 220. As illustrated in FIG. 2B, each of the stators 230 includes coils 231 arranged in sets and disposed around the axis 1-1 of the rotor 220. When the coils are driven using a 3-phase current, they provide a magnetic field which interacts with the magnets of the rotor to turn the rotor around the axis 1-1.

Figure 3:
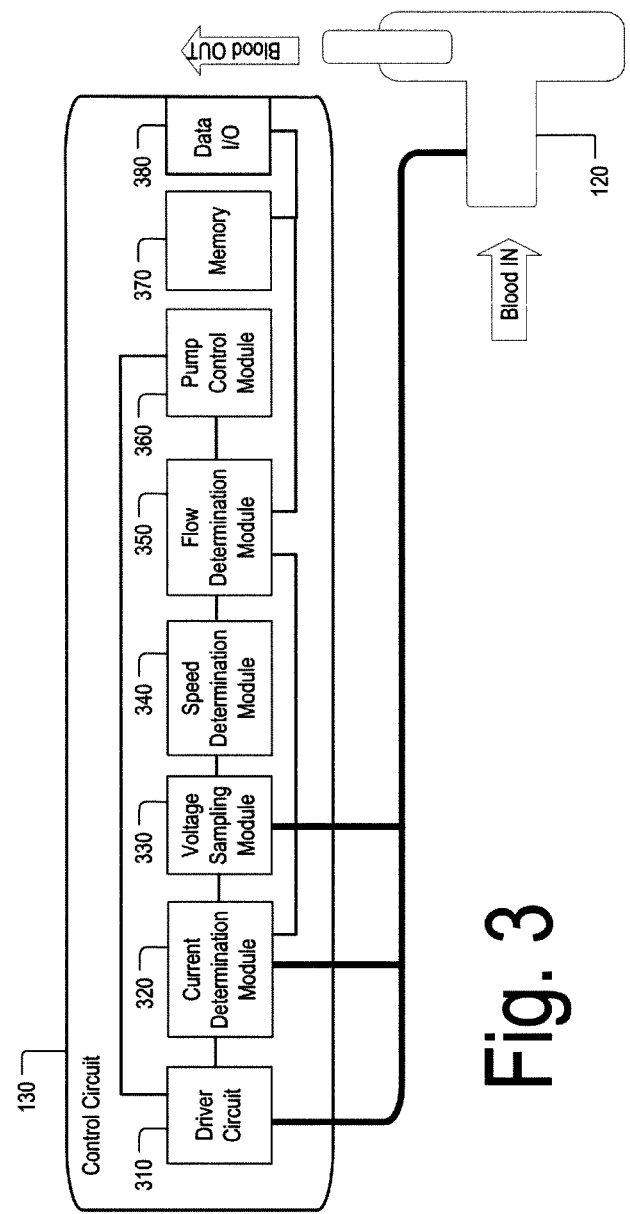
FIG. 3 is a schematic showing of a controller that is part of the blood pump system of FIG. 1.

FIG. 3 depicts a schematic diagram of the control circuit 130. The control circuit 130 comprises driver circuit 310, voltage sampling module 320, current determination module 330, speed determination module 340, flow determination module 350, pump control module 360, and contractility estimation module 370. The modules are depicted and discussed with reference to their individual functions. One or more of the modules 310-370 may be implemented using software operating in a computer system including a general-purpose or special purpose processor, in digital circuitry, or in using analog circuitry.

The driver circuit 310 is an electrical circuit for powering the pump 120 with a 3-phase current. Each phase of the three-phase current preferably is in the form of a generally rectangular wave including alternating off or "open-phase" periods in which power is not applied by the drive circuit and on or "closed-phase" periods during which power is applied. The periods of the various phases are arranged so that at any moment, two sets of coils in a stator of the pump 120 are on or closed-phase and one pair is off or open-phase. The open-phase and closed-phase periods of the various phases are arranged so that the various sets of coils go to an open-phase state in sequence, thus creating the rotating magnetic field that actuates the rotor. Driver circuit 310 applies pulse width modulation during each on or closed-phase period. Thus, during each on or closed-phased period, the voltage applied to the pair of coils varies repeatedly between zero and a selected maximum value at a pulse modulation or chopping frequency much higher than the frequency of the waveform of the repeating closed-phase and open-phase period.

The current determination module 320 may include hardware and/or software for determining the amount of current supplied to the pump. For example, the current determination module may include a known resistance in series with one coil set, and an analog-to-digital converter arranged to sample the voltage across the known resistance so that each such sample represents the instantaneous current passing through the coil pair, as well as an averaging circuit arranged to average these sample to provide a measure of the average current passing through the coil pair.

The control circuit further includes a voltage sampling module 330. The voltage-sampling module may include an analog-to-digital converter connected across one coil set and arranged to capture successive samples of the voltage appearing across the coil set. The voltage-sampling module may also include a digital filter for suppressing variations in the sampled voltage at frequencies at or above the pulse-width modulation or chopping frequency used by the drive circuit, so as to provide a filtered series of values. Alternatively, the sampling circuit may include an analog low-pass filter connected between the A/D converter and the coil pair.

The speed determination module 340 is operatively connected to the voltage sampling module 330 to receive the filtered voltage values that are obtained by that circuit. The speed determination module is arranged to deduce the speed of rotation of the magnetic field, and hence the speed of rotation of the pump's rotor 220, from these values. For example, the speed determination module may be arranged to record the time when the voltage on a coil set drops below the threshold value associated with the open-phase periods as the beginning of an open-phase period, and to calculate the interval between the beginnings of successive open-phase periods. The speed of rotation is inversely proportional to this time. Alternatively, the speed determination module may use the voltage sampling module 330 to measure the voltage across a coil set and detect the back EMF ("BEMF") induced in each one of the coils as they are not being driven. The BEMF is directly proportional to the speed of the rotor. In a further alternative, the speed determination module 340 may determine the time between successive zero crossings of the BEMF signals. The speed of the rotor 220 is inversely proportional to this time.

The flow determination module 350 may include hardware and/or software for determining the rate at which blood is impelled by the pump 120. The flow determination module is operatively connected to current determination module 320 and speed determination module 340 so that the flow determination module 250 receives values representing current and speed of the rotor 120. The flow determination module is arranged to determine the flow rate of blood from the pump based on the current and speed data, as further discussed below with respect to FIG. 4. Pump control module 360 is operatively linked to flow determination module 350 so that the pump control module 360 receives a signal indicating the flow rate from the flow determination module. The pump control module is also linked to driver circuit 310. The pump control module is arranged to control the pump 100 to maintain the pump operating at a predetermined speed set point. In some instances, the pump control module 360 may detect the occurrence of an occlusion or suction event in response to the flow rate of blood exiting the pump 120 falling below a predetermined threshold. In such instances, the pump control module may reduce the speed set point to slow down the pump in order to overcome the ongoing suction or occlusion event. Afterwards, the pump control module may restore the speed set point to the predetermined speed set point.

The memory 370 may be any type of volatile or non-volatile memory, such as RAM, EEPROM, or Flash memory. The memory may be arranged to store blood flow rate estimates that are taken by the flow estimation module. In addition, the memory 370 may be arranged to store timestamps indicating the time when each estimate is taken. The timestamps may be explicitly specified, such as a given value associated with each estimate, or may be implicit in the order in which data is recorded in the memory. Data interface 380 may be a USB, serial, Firewire, or any other type of interface. The data interface may be used to read and write information from the memory 370. In operation, when the data interface 380 is connected to the receiver device 140, blood flow estimates that are made over a period of time (e.g., 24 hours), may be downloaded onto the receiver device. The downloaded data may be presented to a clinician as a time-plot or it may be used to generate and display a contractility index, as discussed with respect to FIG. 1. Furthermore, the data interface 380 may be used to store, into the memory 370, the values for a pump speed set point, for a patient's blood viscosity and for constant coefficients that are part of a model for determining blood flow rate that is used by the flow estimation module 350, as discussed below.

Figure 4:
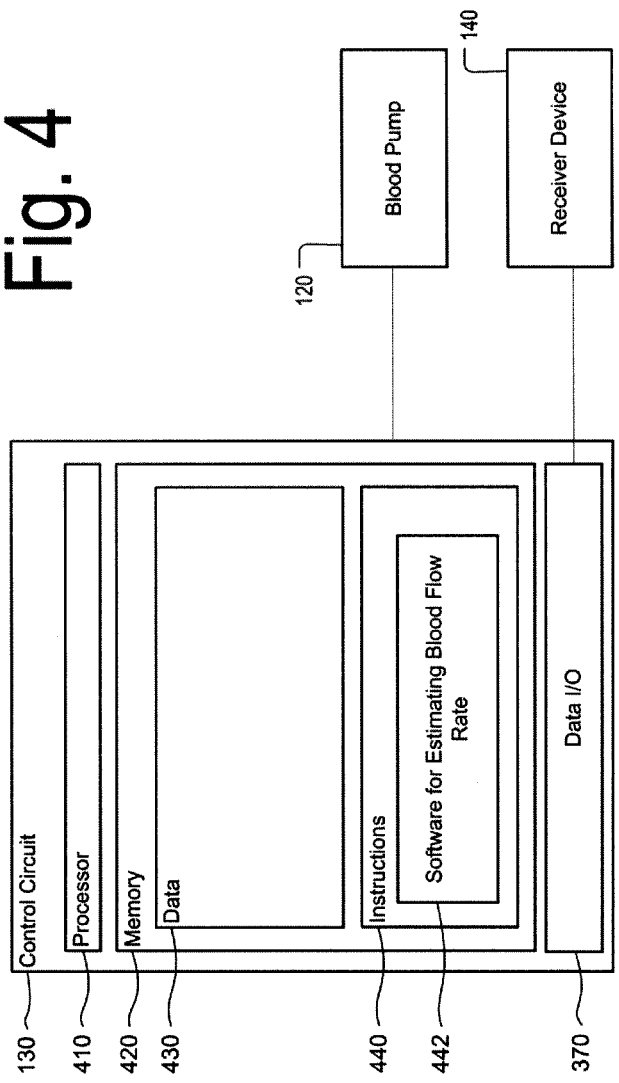
FIG. 4 is a schematic diagram showing the hardware and software used in the blood pump system of FIGS. 1-3.

The various modules discussed above with reference to FIGS. 1-3 desirably are implemented at least in part by a general purpose processor which performs functions associated with the various modules. FIG. 4 depicts this implementation. As shown, the control circuit 130 is implemented using a processor 410, a memory 420, data 430, instructions 440, and the interface 380. Memory 420 stores information accessible by processor 410, including instructions 440 that may be executed by the processor 410. Memory 420 may also include the memory shown as 370 in FIG. 3. The memory also includes data 430 that may be retrieved, manipulated or stored by the processor. The memory may be of any type capable of storing information accessible by the processor, such as a hard-drive, memory card, or any volatile or non-volatile memory. The processor 410 may be any well-known processor, such as commercially available processors. Alternatively, the processor may be a dedicated controller such as an ASIC.

Data 430 may be retrieved, stored or modified by processor 410 in accordance with the instructions 440. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information that is used by a function to calculate the relevant data.

The instructions 440 may be any set of instructions to be executed directly (such as machine code) or indirectly (such as scripts) by the processor. In that regard, the terms "instructions," "steps" and "programs" may be used interchangeably herein. The instructions may be stored in object code format for direct processing by the processor, or in any other computer language including scripts or collections of independent source code modules that are interpreted on demand or compiled in advance.

The instructions 440 include software 442 for determining blood flow rate based on the amount of current used to drive the pump 120 and the speed of rotation of the rotor 220. The software 442 uses a model for determining blood flow rate that is based on the following equations:

$$Q(t) = A(t) - B(t) \tag{1}$$

$$A(t) = aI(t) + bI(t)^2 + cI(t)^3 + d\omega(t) + e\omega(t)^2 + g\omega(t)I(t) + h(\omega(t)^2)I(t) + k \tag{2}$$

$$B(t) = m\frac{d\omega(t)}{dt} \tag{3}$$

$$m = (p*v - q)\omega(t) + r*v + s \tag{4}$$

According to the model, Q(t) corresponds to the instantaneous flow rate of blood exiting the pump 120. The parameter I(t) corresponds to the amount of current supplied to the pump 120 by the control circuit 130. The parameter $\omega(t)$ corresponds to the instantaneous angular velocity of the rotor 220. The parameter $\upsilon$ corresponds to viscosity of the blood. The parameter m is related to the moment of inertia of the rotor 120. The parameters a, b, c, d, e, g, h, k, p, q, r, and s are numerical constants belonging to the set of real numbers. These parameters are fixed for a pump having given characteristics. They can be determined empirically as discussed below. The values of these parameters may be input into the memory 420 by an operator using a keyboard or another input device. Similarly, the value of the parameter "$\upsilon$" may also be entered manually into the memory 420. In an alternative example, the value of the parameter $\upsilon$ may be determined by receiving, by the control circuit 130, user input indicating a patient's hematocrit and using a look-up table to relate the hematocrit to a corresponding viscosity value.

The parameter A(t) models the rate at which blood is impelled by the pump 120 (e.g., flow rate of blood leaving the pump) based on the amount of current used to drive the pump 120 and the speed of the rotor 220. The parameter B(t) accounts for the magnitude of the disturbances in the blood flow rate introduced by the pulsating action of the heart 110. B(t) models the effect of those disturbances either based on the rate of change of the speed of the rotor 220, or based on both the rate of change of the speed of the rotor 220 and viscosity of the patient's blood. Subtracting B(t) from A(t) may result in a more accurate blood flow estimation than using A(t) alone. In some aspects, the parameter B(t) may be thought of as accounting for the dynamic interactions between the fluid (e.g., blood) and the rotor 220. These interactions ultimately bear on the magnitude of the transients in the blood flow that are introduced by the pulsating action of the heart 110.

Although FIG. 4 functionally illustrates the processor and memory as being within the same block, it will be understood that the processor and memory may actually comprise multiple processors and memories that may or may not be stored within the same physical housing. The memory may include one or more media on which information can be stored. Preferably, the medium holding the instructions retains the instructions in non-transitory form. Some or all of the instructions and data may be stored in a location physically remote from, yet still accessible by, the processor. Similarly, the processor may actually comprise a collection of processors which may or may not operate in parallel. Although, in the above example the value of the parameter m is determined using Equation 4, in other examples the value of the parameter m may be determined using the following equation:

$$m = z \cdot \omega(t) + x \qquad (5)$$

The parameters z and x and s are numerical constants belonging to the set of real numbers and they may be specified in the manner discussed with respect to parameters a-k and p-s.

Figure 5:
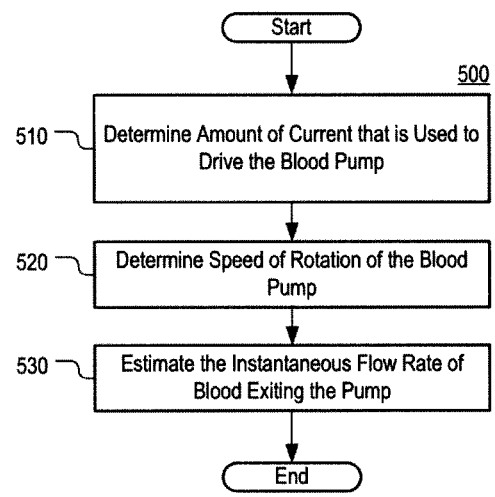
FIG. 5 depicts a flowchart of a method of operation used by the system of FIG. 1.

FIG. 5 depicts a flowchart of a process 500 associated with determining the flow rate of blood exiting the pump 120. At task 510, the amount of current that is used to power the pump 120 is determined by using the current determination module 320. At task 520, the control circuit 130 determines the speed of rotation of the rotor 220. As discussed above the control circuit samples voltage across the coil set 232a and 232b, identifies open-phase periods in which the voltage appearing across the coil is less than a threshold voltage, and determines the number of the open-phase periods per unit time or, equivalently, the time between successive open-phase periods for a particular coil. The control circuit determines the speed based on this measurement. The greater the number of open-phase periods per unit time, or the lesser the time between successive open-phase periods, the faster the speed. At task 530, the control circuit 130 determines instantaneous flow rate of blood exiting the pump 120 based on the amount of current that is used to drive the pump 120 and the speed of the rotor 220. The instantaneous flow rate is determined based on the equation Q(t)=A(t)−B(t) discussed above.

Although, in the above example the process 500 is executed by the control circuit 130, in other examples, the process may be performed by another device. For example, the process 500 may be executed, at least partially, by the processor of a device that is operatively connected to the pump 120 or the control circuit 130. In the latter examples, the device executing the process 500 may not be involved in controlling the operation of the pump 120, but rather it may be a medical device used to passively monitor the state of the heart 110. That device may receive measurements of the amount of current used to drive the pump 120 and the speed of rotation of the rotor 220, and use those measurements to calculate blood flow rate. Each of the measurements may be received from the control circuit 130 or from another source. In another aspect, the process 500 may be executed repeatedly throughout the operation of the pump 120, as part of a control loop or another iterative routine. The process 500 may be executed in real-time or close to real-time.

Figure 6:
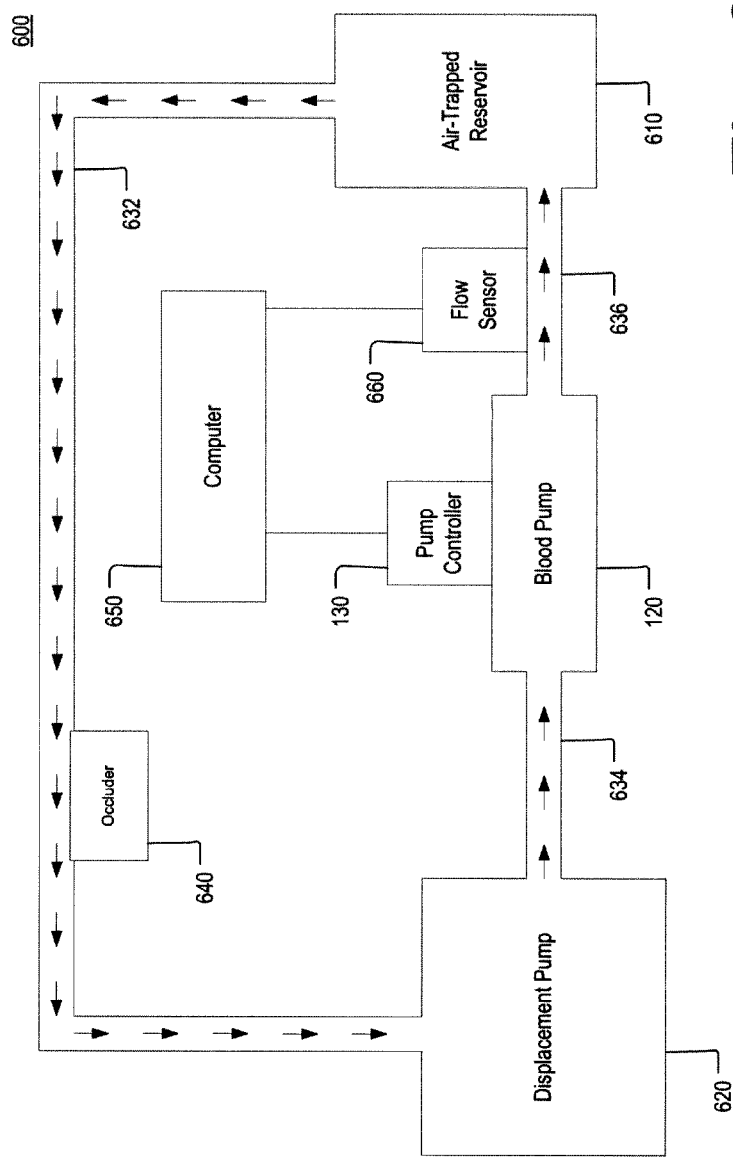
FIG. 6 depicts a flowchart of a test system for determining constants in a model for determining the flow rate of blood out of the pump of FIGS. 2A-B.

The foregoing assumes that the values of the constant coefficients a-k, p-s, and z-x of the model for determining blood flow rate are known. The coefficients may be fixed for particular pump design. They may be determined using the hydraulic circuit 600 that is depicted in FIG. 6. The hydraulic circuit 600 includes a pump 120 of the same design as will be implanted into a patient, an air trapped reservoir 610, a pump 620, tube connections 632-636, and occluder 640. The reservoir 610 may be any vessel capable of holding fluids and being pressurized to 100 mmHg. The pump 620 is a displacement pump having a piston driven by a linear actuator, such as Model V455, manufactured by Ling Dynamics Systems, Middletown, Wis., USA. The tube connections 532-536 are PVC tubes having between ½ and ⅜ inch inner diameter. The occluder 640 is a proportional valve. The inlet of the pump 620 is coupled to the reservoir 610 via tube connections 632. The outlet of the pump 620 is coupled to the inlet tube of the pump 120. The outlet end of the pump 120 is also coupled to the reservoir 610 thus closing the circuit 600 and allowing fluid to circulate from the reservoir 610 through the pump 620 and the pump 120 back to the reservoir 610. The occluder 640 is mounted on one of the tube connections 532-536 and it may be used to vary the hydraulic resistance of the circuit 600.

The computer 650 may be connected to the control circuit 130 and the flow sensor 660. The flow sensor 640 is an ultrasonic transducer, such as model H11XL, manufactured by Transonic Systems Inc., of Ithaca, N.Y., USA. The computer 650 collects pump data from the control circuit 130, as well as data measured by the sensor 660. The pump data includes the amount of current used to drive the pump 120 and the speed of rotation of the rotor 220. The data from the sensor 660 indicates the flow rate of fluid exiting the pump 120.

In operation, the reservoir 610 is filled with glycerin-water mixture that mimics blood viscosity of about 2 cP, 3 cP, and 4 cP at 37 C and about 1 L of air is left in the reservoir. After the reservoir is filled with the water-glycerin mixture, the circuit 600 is pressurized to about 100 mmHg. Afterwards, the pump 120 is run, as it would when it is used in vivo, drawing the glycerin-water mixture from the reservoir 610, running it across the tube connections 532-536, and returning it back into the reservoir 610, afterwards. While the pump 120 is operated, the displacement pump 610 is used to modify the pressure head on the inlet end of the pump 120 in similar way as the heart 110 would in the system 100. Furthermore, while the pump 120 is run, the computer 650 collects pump data from the control circuit 130 and flow data from the sensor 660. Afterwards, the computer 650 may determine the various coefficients in the model for determining blood flow (i.e., Equation 1) by utilizing various minimization techniques for minimizing the error between the measured flow and the flow calculated using the model based on the pump data collected by the computer 560. Furthermore, the data collected by the computer 650 may be used to calculate transfer functions for models used for determining the flow rate of blood.

Figure 7:
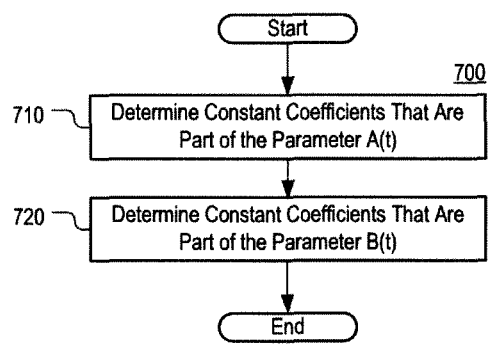
FIG. 7 depicts a flowchart of a process associated with using the test set-up depicted in FIG. 6.

FIG. 7 depicts a flowchart of a process 700 associated with using the hydraulic circuit 600 to determine the coefficients in the model for determining blood flow rate (e.g., equation 1). As discussed above, the model is expressed by the equation Q(t)=A(t)−B(t).

At task 710, the coefficients a, b, c, d, e, g, h, and k that are part of the parameter A(t) are determined. The pump 120 is run while the displacement pump 510 is left inactive. The resistance of the circuit 800 is varied, using the occluder 540, in 8 steps between a closed and fully opened lumen. This procedure is repeated for 12 rotational speeds from 1.8 to 4 krpm in steps of 200 rpm of the rotor of the pump 120. Pump data, as well as data from the flow sensor 530, is acquired as soon as a steady state of the flow rate of the water-glycerin fluid out of the pump 120 is reached. These experiments are repeated with 3 different viscosities of about 2, 3, and 4 cP of the water-glycerin mixture. A warming bath can be used to control the fluid temperature and therefore to keep the viscosity stable. Once the pump data and flow data is collected from all experiments, the relationship between speed, current and flow is determined based on the collected data. The relationship may be determined by employing surface fits over the whole current-speed-flow range and for all viscosities.

At task 720, the coefficients in the parameter B(r) are determined. More particularly, the sub-coefficients {n and o} or {p, q, r, and s} are determined, depending on whether equation 4 or Equation 5 is used to calculate the parameter m that is part of B(t). The displacement pump 510 is current-controlled, permitting a very fast control of the pump dynamics with the generation of broadband pressure signals. The displacement pump 510 is driven using a variable frequency signal. The variable frequency signal is a linear sinusoidal sweep ranging from 0.1 to 20 Hz over 250 sec. The sweep signal is repeated at different speeds of the pump 120 that are manually changed from 2 to 4 krpm in stepwise increments of 400 rpm. All measurements are repeated with the hydraulic resistance in two different states, thus resulting in 12 test signal sets. The resistance is adjusted with the displacement pump inactive and for a speed of the pump 120 ranging from 2 krpm to 4 krpm in order to have a measured flow ranging from 5 l/min to 11 l/min in a low resistance state and from 3 l/min to 7 l/min in a high resistance state. These experiments are repeated with 3 different viscosities of about 2, 3, and 4 cP resulting in 36 datasets. As the experiments are performed both pump data and flow data is collected by the computer 650. Afterwards, the coefficients {n and o} or {p, q, r, and s} are identified by minimizing the sum between the squared errors between the measured flow of fluid out of the pump 120 and the flow estimated using the model Q(t)=A(t)-B(t). The minimization may be performed using a simplex search optimization method. Although in this example the coefficients {n and o} or {p, q, r, and s} are approximated and then used to calculate the coefficient m, in other examples the coefficient in may be approximated directly. In one example, the following coefficient values may be determined: x=-2.95*10$^{-7}$, z=0.0018, p=3.379*10$^{-3}$, q=3.543*10$^{-7}$, r=-1.688*10$^{-4}$, s=2.13*10$^{-3}$.

Figure 8:
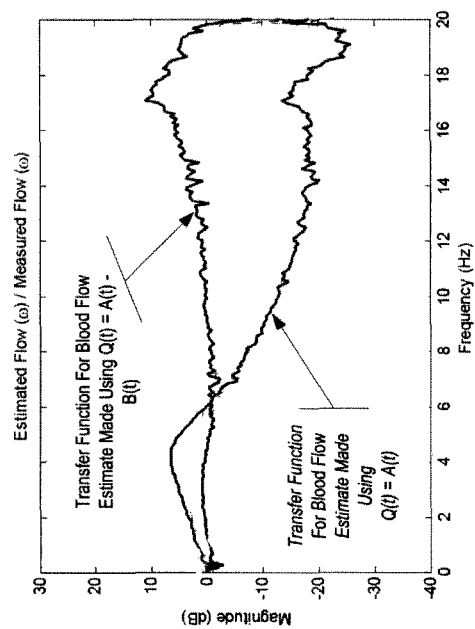
FIG. 8 depicts a plot of the transfer functions for blood flow estimates.

FIG. 8 depicts a plot of the transfer functions for blood flow estimates calculated using the equations A(t) and A(t)-B(t). Each plot is determined by taking the median of twelve different data sets collected using the test setup discussed with respect to FIG. 6. Each data set is determined by running the circuit 600 with different combination of settings (e.g., different resistance imparted by the occluder 640, different speed of the pump 120, different viscosities of the water-glycerin mixture, etc.). Thus, the two plots show the frequency domain decomposition of the median transfer functions for A(t) and A(t)-B(t), respectively, and show that blood flow rate estimates taken using the equation Q(t)=A(t)-B(t) have a higher bandwidth than blood flow estimates taken using the equation Q(t)=A(t).

As illustrated, the blood flow estimate calculated using the formula A(t) has an underdamped response with a peak occurring at 4 Hz and cutoff at about 5 Hz. By contrast, the blood flow estimate calculated using A(t)-B(t) has a cutoff at about 15 Hz. Stated succinctly, using the acceleration of the rotor of the pump 120 and the parameter m when calculating the flow rate of blood exiting the pump 120 results in an estimate having a broader dynamic range. The broader dynamic range enables the detection of transient variations in the blood flow rate that result from the pulsating action of the heart. As discussed above, these variations may be used to determine various parameters related to the contractility of the heart 110 which, in turn, can be used subsequently by clinicians to evaluate the heart's health.

FIGS. 5 and 7 are provided as examples. At least some of the tasks associated with FIGS. 5 and 7 may be performed in a different order than represented, performed concurrently or altogether omitted. Although, in the above examples, the model of determining blood flow rate is implemented using software, in other examples it may be implemented using custom-made digital logic (e.g., FPGA), or any combination of digital logic and software. As these and other variations and combinations of the features discussed above can be utilized without departing from the subject matter as defined by the claims, the foregoing description of exemplary aspects should be taken by way of illustration rather than by way of limitation of the subject matter as defined by the claims. It will also be understood that the provision of the examples described herein (as well as clauses phrased as "such as," "e.g.," "including" and the like) should not be interpreted as limiting the claimed subject matter to the specific examples; rather, the examples are intended to illustrate only some of many possible aspects.

The invention claimed is:
1. A blood pump system comprising:
  a pump including a housing and a rotor disposed within the housing, the rotor being rotatable around an axis; and
  a control circuit operatively coupled to the pump, the control circuit being configured to:
  determine a speed of rotation of the rotor;
  determine a derivative of the speed of rotation of the rotor;
  determine a flow rate of blood exiting the pump, the determined blood flow rate having a dynamic frequency range of at least 15 hertz based at least in part on a calculated time-varying parameter which accounts for disturbances in the blood flow rate introduced by the pulsating action of the heart, the time-varying parameter based at least in part on the derivative of the speed of rotation.

2. The blood pump system of claim 1, wherein the control circuit is further configured to:
  determine an amount of current that is used to drive the pump;
  wherein the blood flow rate is determined based on the amount of current and the speed of rotation of the rotor.

3. The blood pump system of claim 1, wherein the control circuit is further configured to:
  receive user input indicating a viscosity of the blood;
  wherein the blood flow rate is further determined based on the indicated viscosity.

4. The blood pump system of claim 1, wherein the blood flow rate is determined based on the equation:

$$Q(t) = aI(t) + bI(t)^2 + cI(t)^3 + d\omega(t) + e\omega(t)^2 + g\omega(t)I(t) + h(\omega(t)^2)I(t) + k - m\frac{d\omega(t)}{dt}$$

wherein:
  Q(t) is a blood flow rate,
  I(t) is amount of current used to drive the pump;
  ω(t) is speed of the rotor;
  a, b, c, d, e, g, h, and k are constants belonging to the set of real numbers, and m is a coefficient that depends on the speed of the pump rotor.

5. The blood pump system of claim 4, wherein the value of the coefficient m is calculated using the formula:

$$m = n*\omega(t) + o$$

wherein n and o are constants belonging to the set of real numbers.

6. The blood pump system of claim 4, wherein the value of the coefficient m is calculated using the formula:

$$m=(p*v-q)\omega(t)+r*v+s$$

wherein:
p, q, r, and s are constants belonging to the set of real numbers, and
v is viscosity of a patient's blood.

7. The blood pump system of claim 4, wherein the control circuit is configured to receive user input indicating the values of at least some of the coefficients a, b, c, d, e, g, h, and k.

8. The blood pump system of claim 1, wherein the control circuit is further configured to transmit an indication of the determined blood flow rate to a remote device.

9. The blood pump system of claim 1, wherein the control circuit is further configured to determine a parameter related to contractility of a patient's heart based on the blood flow rate.

10. The blood pump system of claim 9, wherein the control circuit is configured to determine the parameter related to the contractility of the patient's heart using the determined flow rate having the dynamic frequency range of at least 15 hertz.

11. The blood pump system of claim 8, wherein the determined parameter is based on a rate of change of pressure head across the pump, the rate of change being determined based on the blood flow rate.

12. A method for determining a flow rate of blood that is used to provide a ventricular assistance to a patient's heart:
determining a speed of rotation of a rotor of the pump;
determining a derivative of the speed of rotation of the rotor; and
calculating, by a processor, the flow rate of the blood having a dynamic frequency range of at least 15 hertz based at least in part on a calculated time-varying parameter which accounts for disturbances in the blood flow rate introduced by the pulsating action of the heart, the time-varying parameter based at least in part on the derivative of the speed of rotation.

13. The method of claim 12, further comprising:
determining an amount of current used to drive the pump;
wherein the blood flow rate is calculated also based on the amount of current.

14. The method of claim 12, wherein the time-varying parameter is calculated also based on the viscosity of the blood and the speed of rotation of the rotor.

15. The method of claim 12, wherein
the blood flow rate is calculated using the equation:

$$Q(t) = aI(t) + bI(t)^2 + cI(t)^3 + d\omega(t) + e\omega(t)^2 + g\omega(t)I(t) + h(\omega(t)^2)I(t) + k - m\frac{d\omega(t)}{dt}$$

wherein:
Q(t) is a blood flow rate,
I(t) is amount of current used to drive the pump;
ω(t) is speed of the rotor;
a, b, c, d, e, g, h, and k are constants belonging to the set of real numbers, and
m is a coefficient that depends on the speed of the pump rotor.

16. The method of claim 15, wherein the value of the coefficient m is calculated using the formula:

$$m=n*\omega(t)+o, \text{ and}$$

n and o are constants belonging to the set of real numbers.

17. The method of claim 15, wherein the value of the coefficient m is calculated using the formula:

$$m=(p*v-q)\omega(t)+r*v+s$$

wherein:
p, q, r, and s are constants belonging to the set of real numbers, and
v is viscosity of the patient's blood.

18. The method of claim 15, wherein the values of the coefficients a, b, c, d, e, g, h, and k are specified via user input.

19. The method of claim 12, further comprising determining a rate of pressure change of blood across the pump based on the determined flow rate.

20. The method of claim 12, further comprising determining a parameter related to the contractility of the patient's heart.

21. The method of claim 20, wherein the determining the parameter related to the contractility of the patient's heart is performed using the calculated flow rate having the dynamic frequency range of at least 15 hertz.

* * * * *